(12) United States Patent
Richards et al.

(10) Patent No.: US 8,840,590 B2
(45) Date of Patent: Sep. 23, 2014

(54) SAFETY PEN NEEDLE ASSEMBLY

(75) Inventors: Stephen Lynn Richards, Holdrege, NE (US); Tieming Ruan, Randolph, NJ (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 431 days.

(21) Appl. No.: 12/866,779

(22) PCT Filed: Feb. 5, 2009

(86) PCT No.: PCT/US2009/033204
§ 371 (c)(1),
(2), (4) Date: Mar. 8, 2011

(87) PCT Pub. No.: WO2009/102612
PCT Pub. Date: Aug. 20, 2009

(65) Prior Publication Data
US 2011/0178473 A1    Jul. 21, 2011

Related U.S. Application Data

(60) Provisional application No. 61/029,133, filed on Feb. 15, 2008.

(51) Int. Cl.
*A61M 5/32* (2006.01)
*A61M 5/34* (2006.01)

(52) U.S. Cl.
CPC .............. *A61M 5/3257* (2013.01); *A61M 5/347* (2013.01); *A61M 2005/3254* (2013.01); *A61M 2005/3247* (2013.01)
USPC .......................................... 604/198; 604/192

(58) Field of Classification Search
USPC .......... 604/192, 195, 197, 198, 181, 187, 263
See application file for complete search history.

(56) References Cited

U.S. PATENT DOCUMENTS

| 4,921,491 A | 5/1990 | Champ |
| 5,964,739 A | 10/1999 | Champ |

(Continued)

FOREIGN PATENT DOCUMENTS

| EP | 0409180 A1 | 1/1991 |
| EP | 1949928 A1 | 7/2008 |

(Continued)

*Primary Examiner* — Kevin C Sirmons
*Assistant Examiner* — Shefali Patel
(74) *Attorney, Agent, or Firm* — Hoffmann & Baron, LLP (57) ABSTRACT

A safety pen needle assembly is provided herein which includes a tubular carrier (12) having a distal end, a proximal end and a transverse engagement wall (30) located between the proximal and distal ends. The engagement wall includes an aperture (32). A needle (16) is further provided having a distal end, for injection into a patient, and a proximal end, along with a needle hub (14). The needle is fixed to the needle hub so as to move therewith, and the needle hub is disposed in the carrier distally of the engagement wall. The assembly also includes a shield (18) for selectively covering the distal end of the needle. A first biasing element (20) is provided for urging the needle hub from a first hub position where the needle extends through the aperture of the engagement wall to a second hub position where the proximal end of the needle is located distally of a proximally-facing outer surface of the engagement wall. In addition, a second biasing element (22) is provided for urging the shield from a first shield position where the distal end of the needle is not covered by the shield to a second shield position where the distal end of the needle is covered by the shield.

3 Claims, 12 Drawing Sheets

(56) References Cited

U.S. PATENT DOCUMENTS

| | | |
|---|---|---|
| 7,540,858 B2 * | 6/2009 | DiBiasi .................. 604/192 |
| 2003/0014018 A1 | 1/2003 | Giambattista et al. |
| 2005/0288607 A1 | 12/2005 | Konrad |

FOREIGN PATENT DOCUMENTS

| | | |
|---|---|---|
| FR | 2654346 A1 | 5/1991 |
| WO | 2004030539 A1 | 4/2004 |

* cited by examiner

SAFETY PEN NEEDLE ASSEMBLY

This application is a National Stage Application under 35 U.S.C. §371 of PCT Application No. PCT/US2009/033204, filed Feb. 5, 2009, which claims priority to U.S. Provisional Patent Application No. 61/029,133, filed Feb. 15, 2008.

FIELD OF THE INVENTION

This invention relates to pen needle assemblies for pen injectors and, more particularly, to safety pen needle assemblies.

Safety pen needle assemblies are known in the prior art. These assemblies are configured to shield a distal, or patient, end of a needle, particularly after use. A pen needle, however, is double ended, with an exposed proximal end for insertion into a septum of a drug cartridge for accessing the contents of the drug cartridge. In general, the prior art does not provide a mechanism for shielding the proximal, or non-patient, end of the needle.

SUMMARY OF THE INVENTION

A safety pen needle assembly is provided herein which includes a tubular carrier having a distal end, a proximal end and a transverse engagement wall located between the proximal and distal ends. The engagement wall includes a proximally-facing outer surface and an aperture formed through the engagement wall. A needle is further provided having a distal end, for injection into a patient, and a proximal end, along with a needle hub. The needle is fixed to the needle hub so as to move therewith, and the needle hub is disposed in the carrier distally of the engagement wall. The assembly also includes a shield for selectively covering the distal end of the needle. A first biasing element is provided for urging the needle hub from a first hub position where the needle extends through the aperture of the engagement wall to a second hub position where the proximal end of the needle is located distally of the proximally-facing outer surface of the engagement wall. In addition, a second biasing element is provided for urging the shield from a first shield position where the distal end of the needle is not covered by the shield to a second shield position where the distal end of the needle is covered by the shield. Advantageously, with the subject invention, an assembly is provided which shields both the proximal and distal ends of a pen needle.

These and other features of the invention will be better understood through a study of the following detailed description and accompanying drawings.

DETAILED DESCRIPTION OF THE INVENTION

Figure 1:
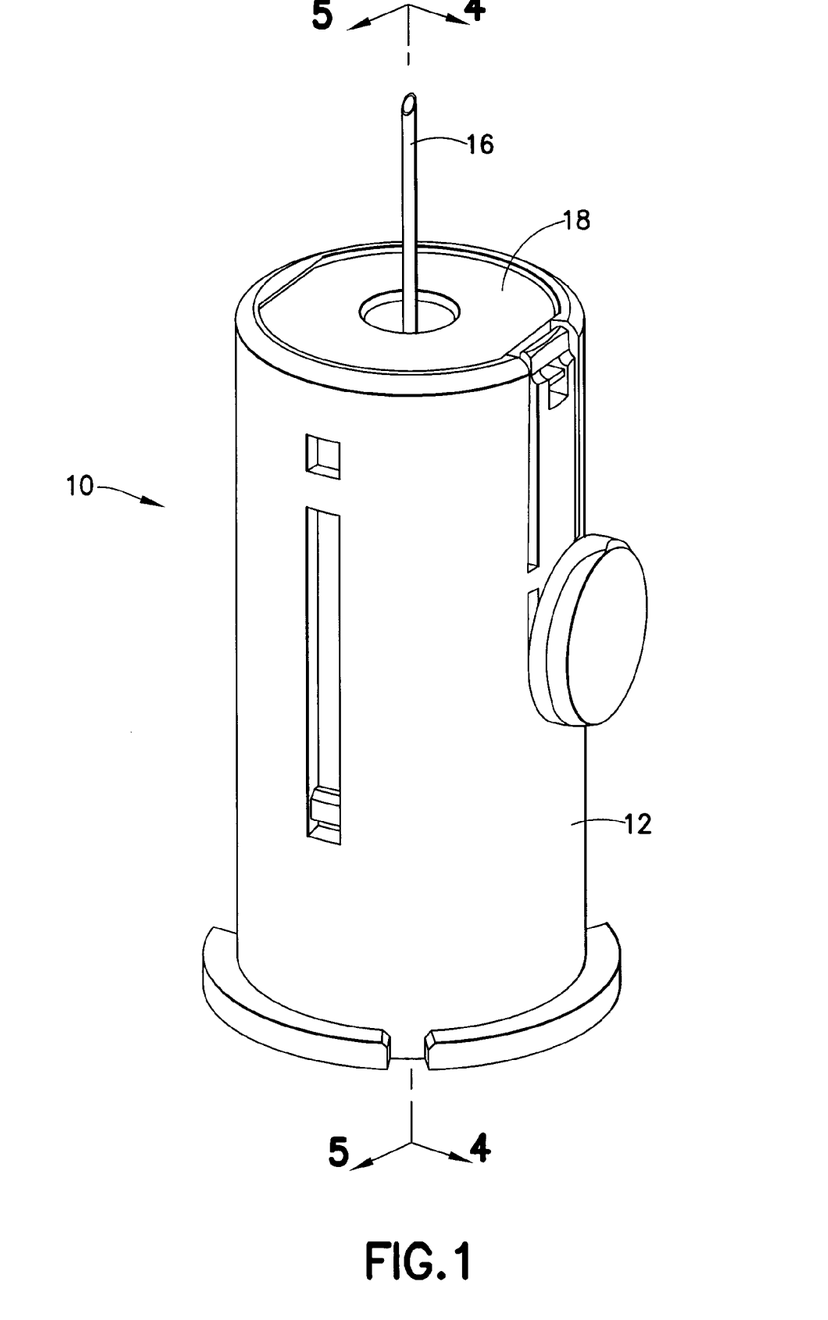
FIG. 1 is a perspective view of a safety pen needle assembly formed in accordance with the subject invention.
Figure 2:
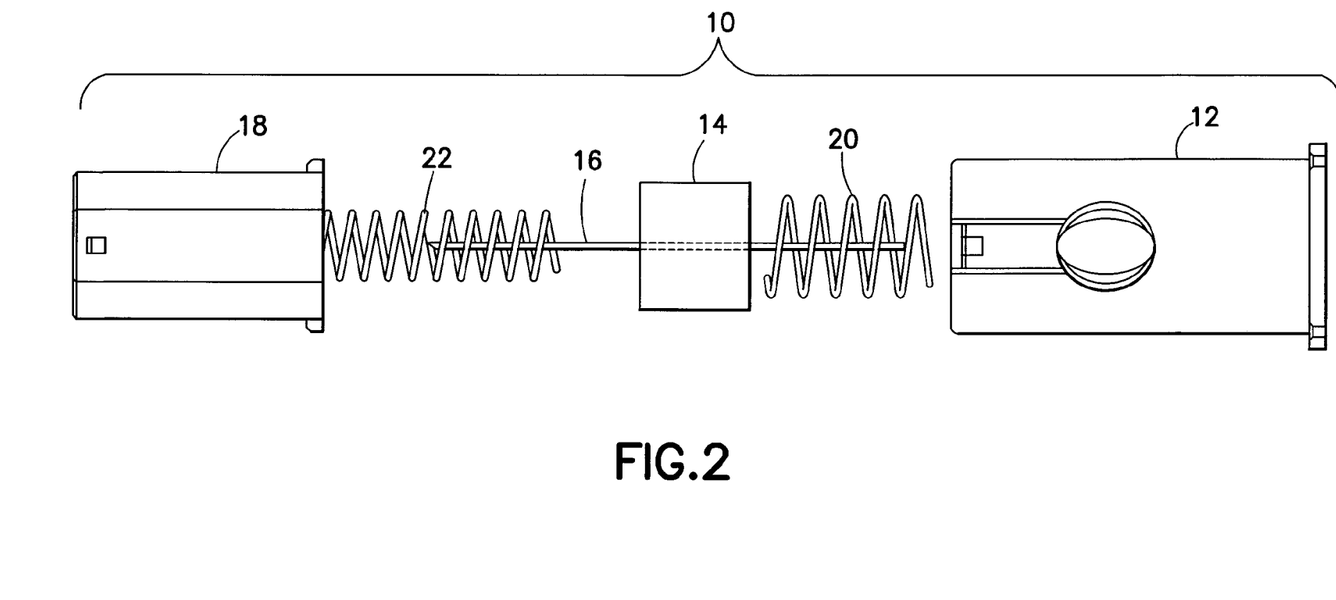
FIG. 2 is an exploded view of a safety pen needle assembly formed in accordance with the subject invention.
Figure 3:
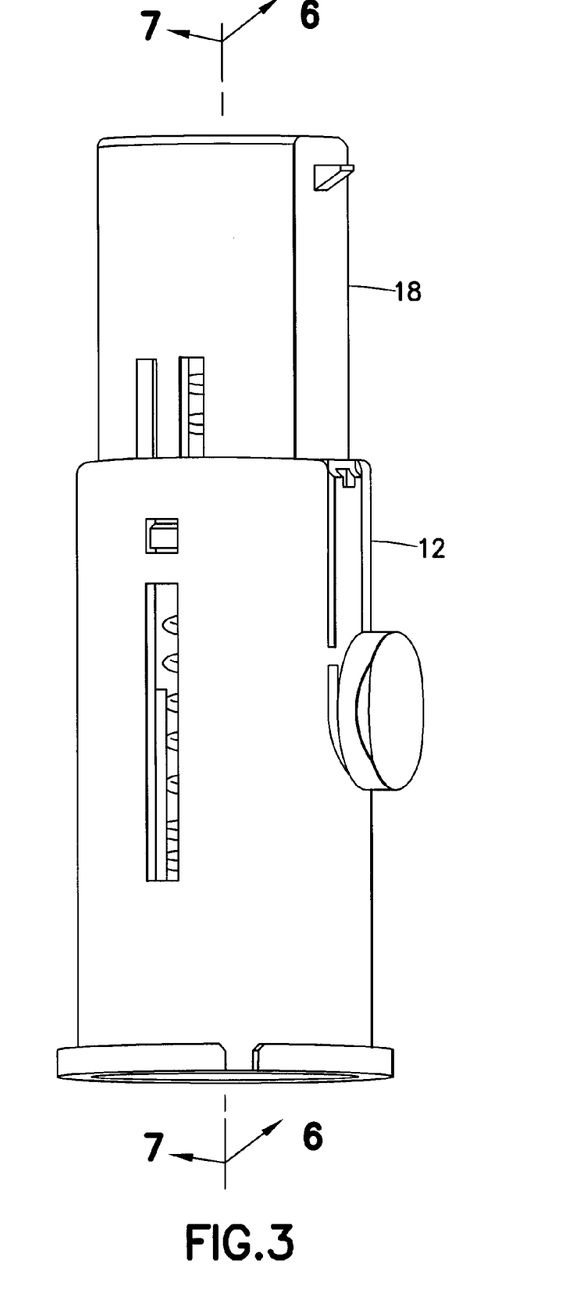
FIG. 3 is a side elevational view of the safety pen needle assembly formed in accordance with the subject invention shown in a shielded position.

With reference to FIG. 1, a safety pen needle assembly 10 is shown prior to use. As shown more clearly in FIG. 2, the assembly 10 generally includes a carrier 12, a needle hub 14, to which is fixed a needle 16, a shield 18, a first biasing element 20 and a second biasing element 22. The components of the assembly 10 are cooperatively arranged to allow for shielding of the needle 16, as shown in FIG. 3.

With reference to FIGS. 4-10, the carrier 12 includes a sidewall 24 that is generally tubular and extends from a distal end 26 to a proximal end 28. An engagement wall 30 is disposed transversely within the carrier 12. An aperture 32 is formed in the engagement wall 30, preferably in the center thereof. It is preferred that the carrier 12 be provided with features 34 (e.g., threads and/or luer connector) for removably mounting the carrier 12 onto a pen injector. It is further preferred that the features 34 be disposed proximally of the engagement wall 30.

The needle 16 is a pen injector needle and includes a distal end 36 for injection into a patient. The needle 16 also includes an opposite proximal end 38 which may be used to pierce the septum of a medical cartridge to obtain access to medical contents contained therein. The needle 16 is fixed to the needle hub 14 so that the needle 16 moves in concert with the needle hub 14. A channel 15 (FIGS. 13 and 14) may be formed through the needle hub 14 in which the needle 16 is seated and fixed (e.g., adhesively attached).

Figure 4:
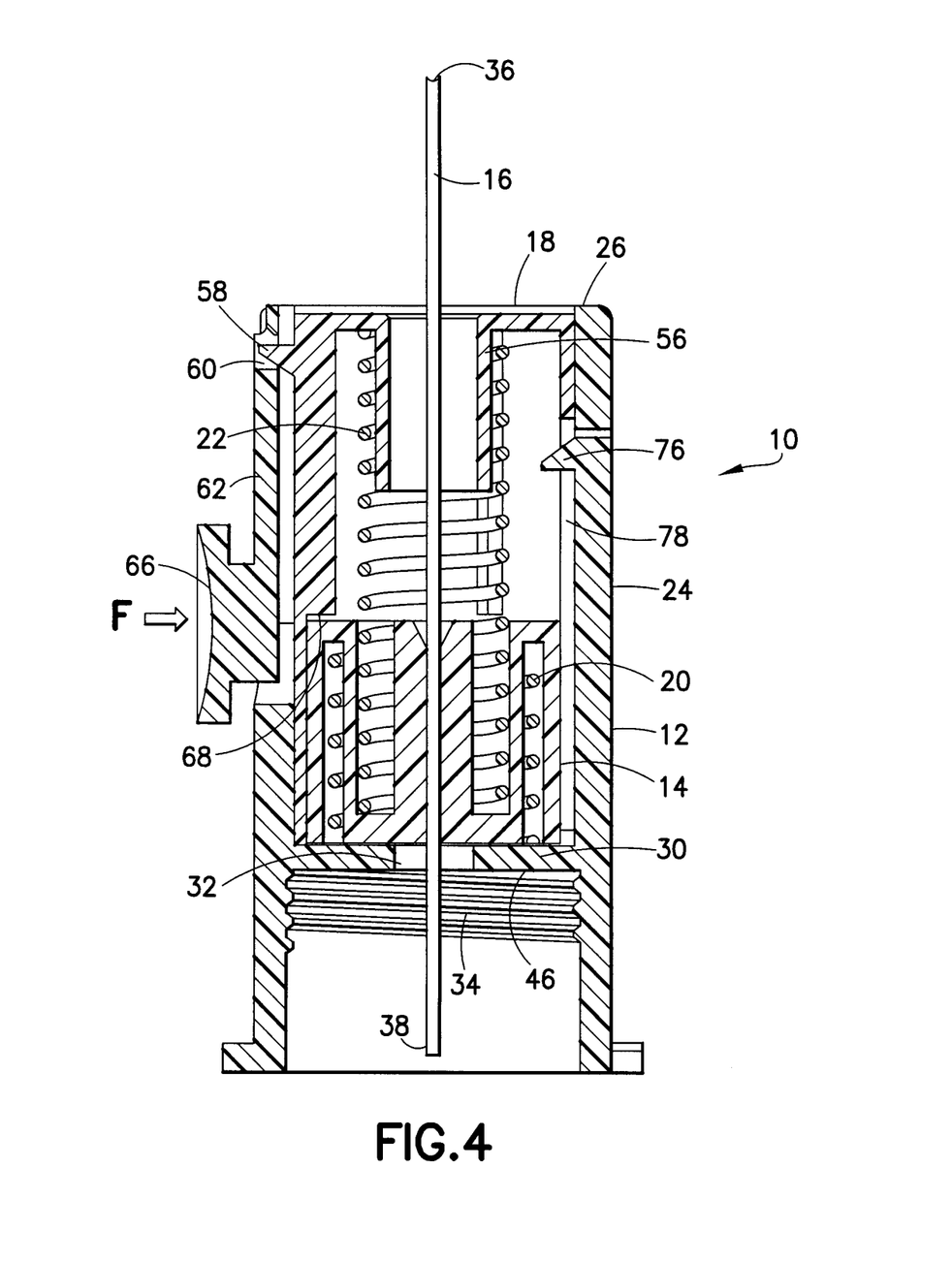
FIG. 4 is a cross-sectional view taken along line 4-4 of FIG. 1.
Figure 5:
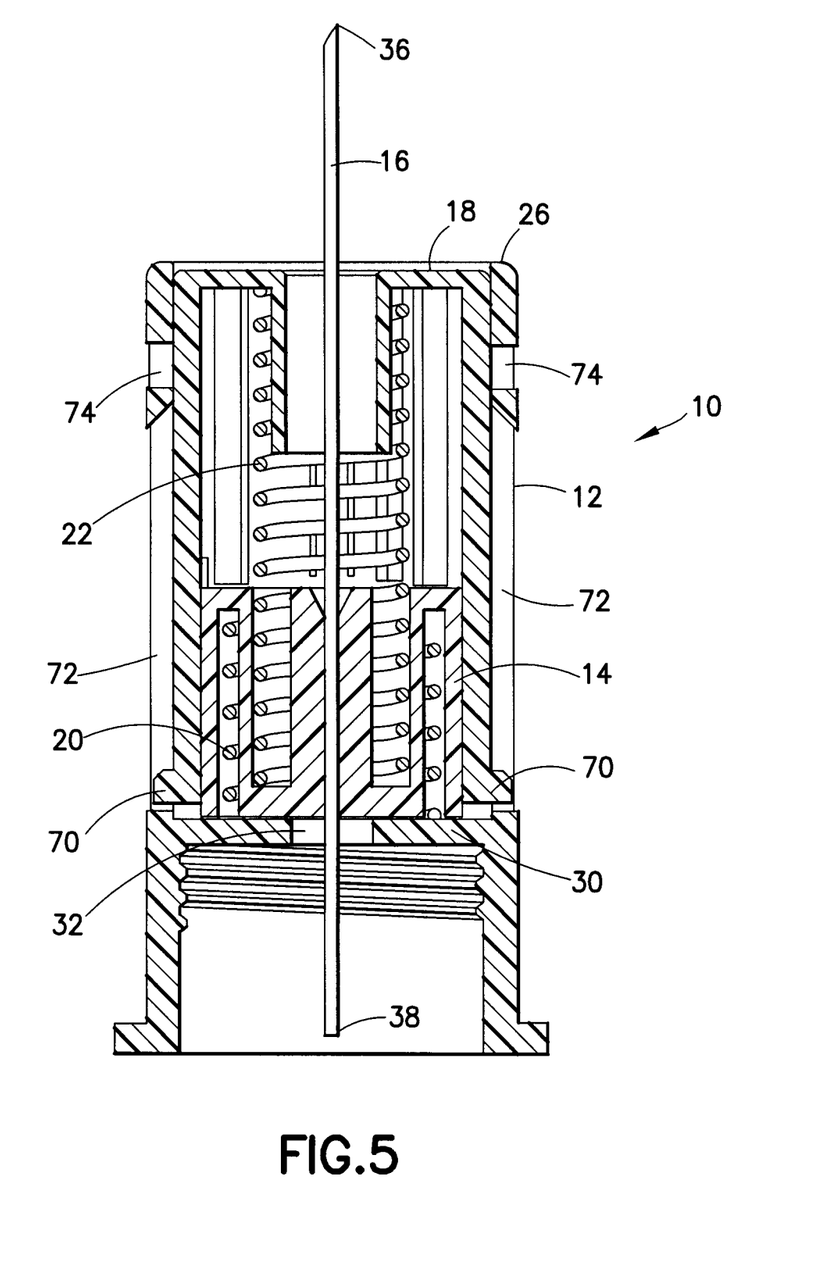
FIG. 5 is a cross-sectional view taken along line 5-5 of FIG. 1.

As best shown in FIGS. 5-8, the needle hub 14 is disposed distally of the engagement wall 30. In an initial state, as shown in FIGS. 4 and 5, the needle 16 extends through the aperture 32 formed in the engagement wall 30. In the initial state, the proximal end 38 of the needle 16 is located so as to be inserted sufficiently into a drug cartridge to obtain proper access therein. Access into a drug cartridge is obtained by mounting the assembly 10 onto a pen injector (e.g., using the features 34) causing the proximal end 38 of the needle 16 to move proximally into the pen injector and to pierce the septum of a drug cartridge contained within the relevant pen injector.

Figure 6:
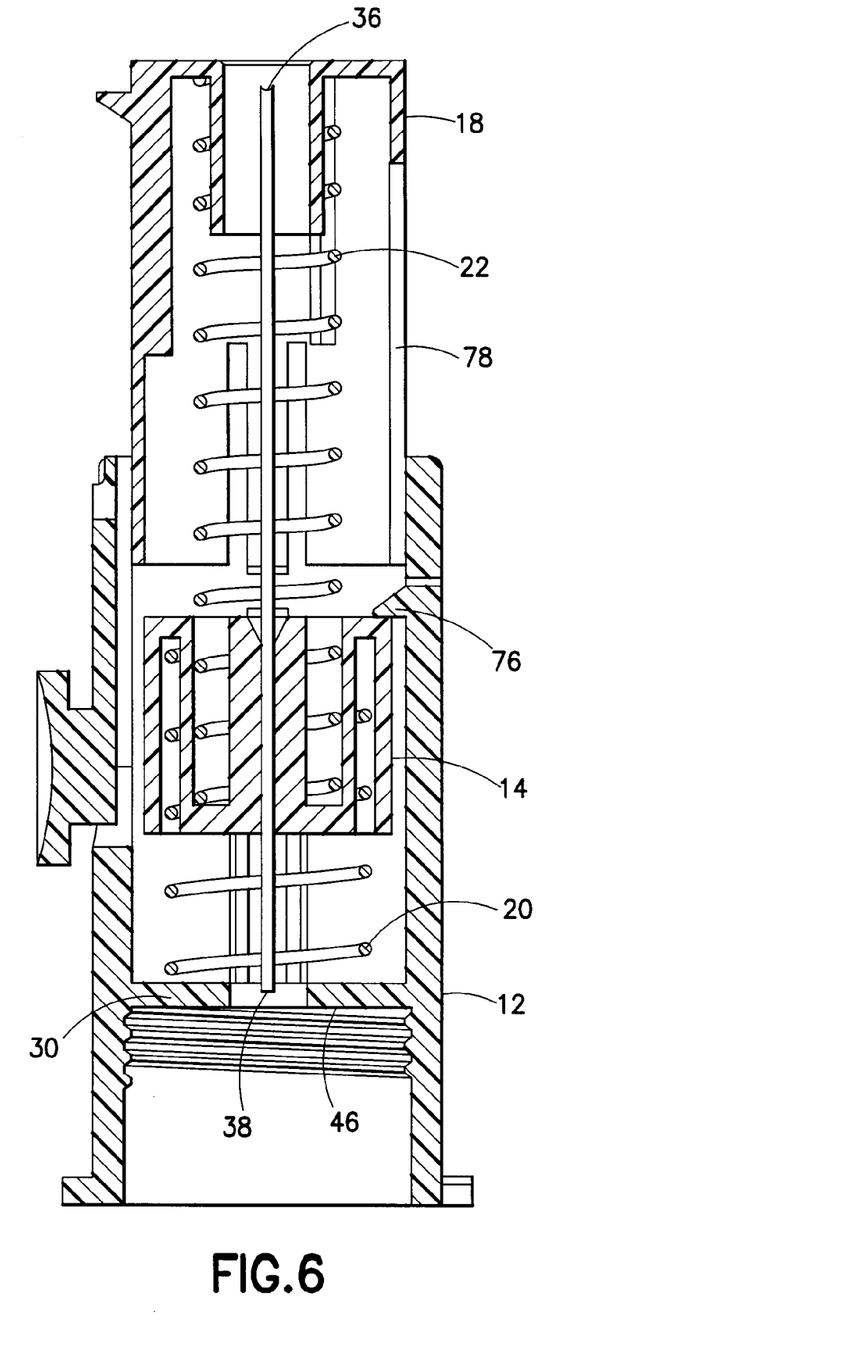
FIG. 6 is a cross-sectional view taken along line 6-6 of FIG. 3.
Figure 7:
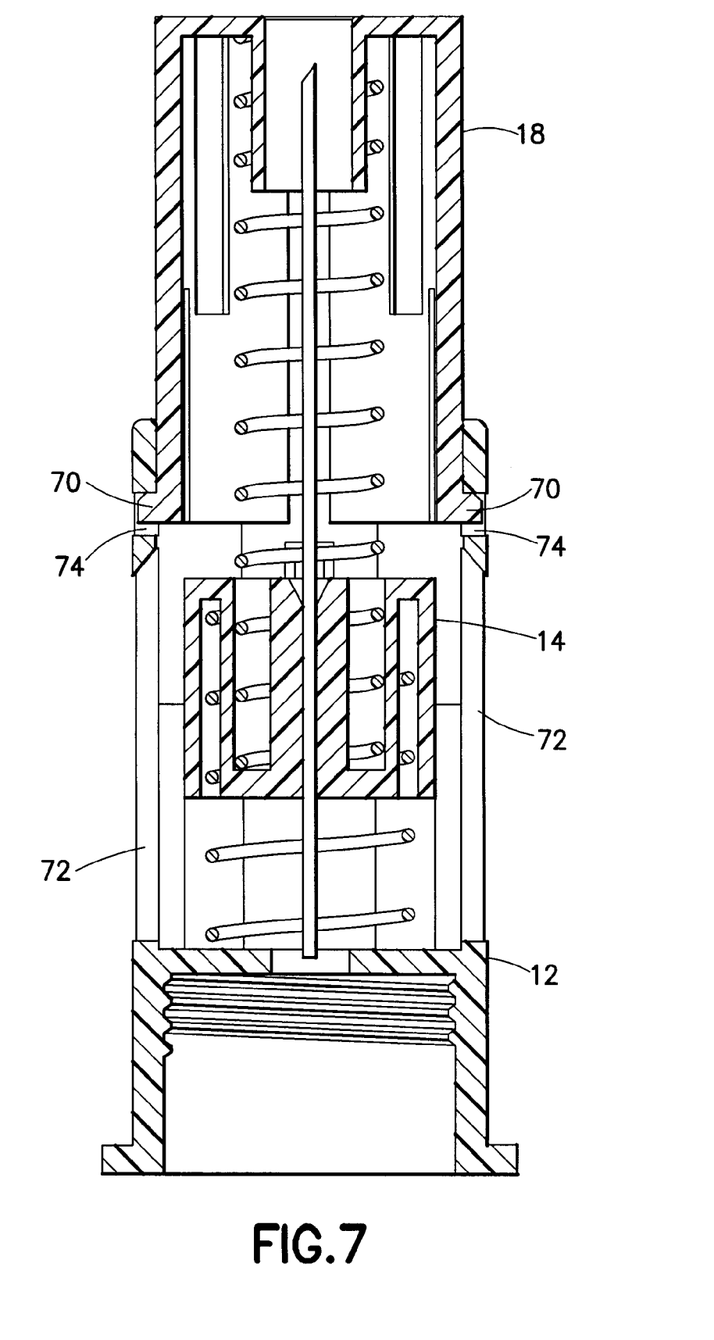
FIG. 7 is a cross-sectional view taken along line 7-7 of FIG. 3.
Figure 8:
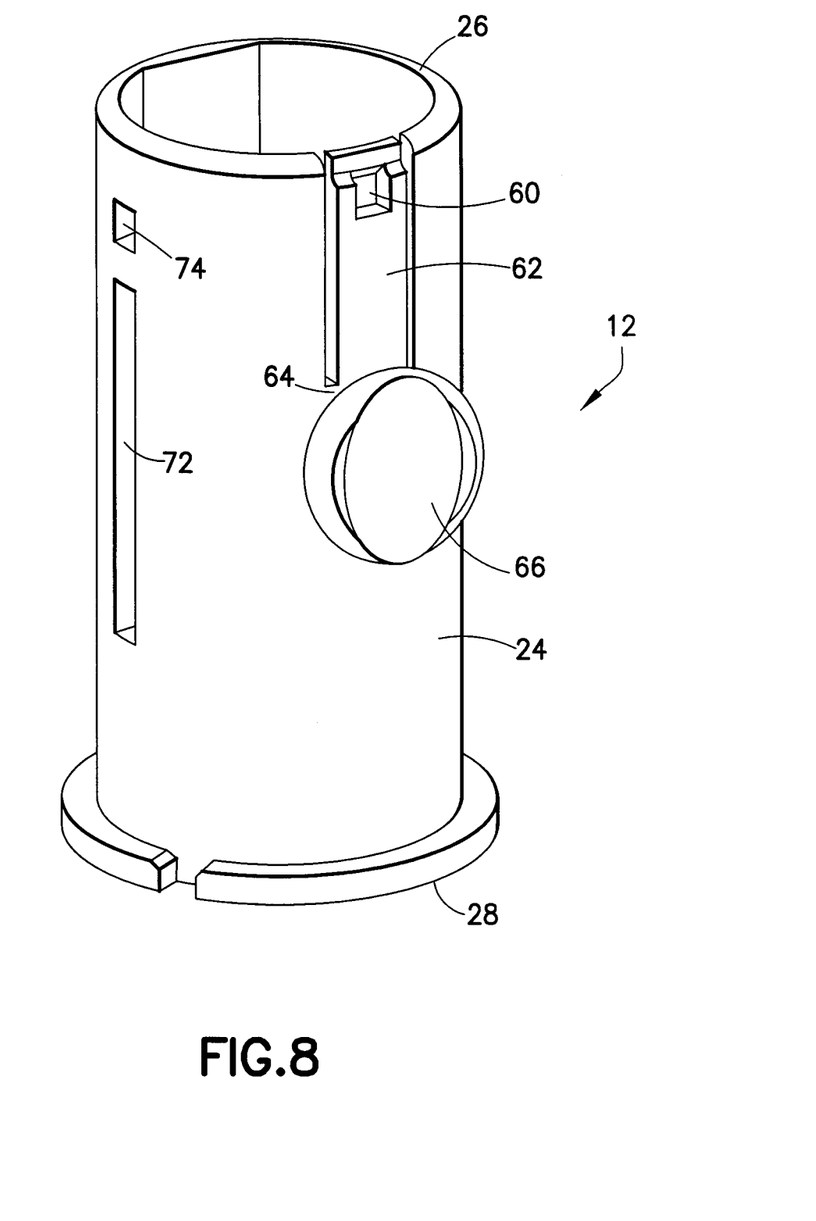
FIGS. 8-10 are different views of a carrier usable with the subject invention.
Figure 9:
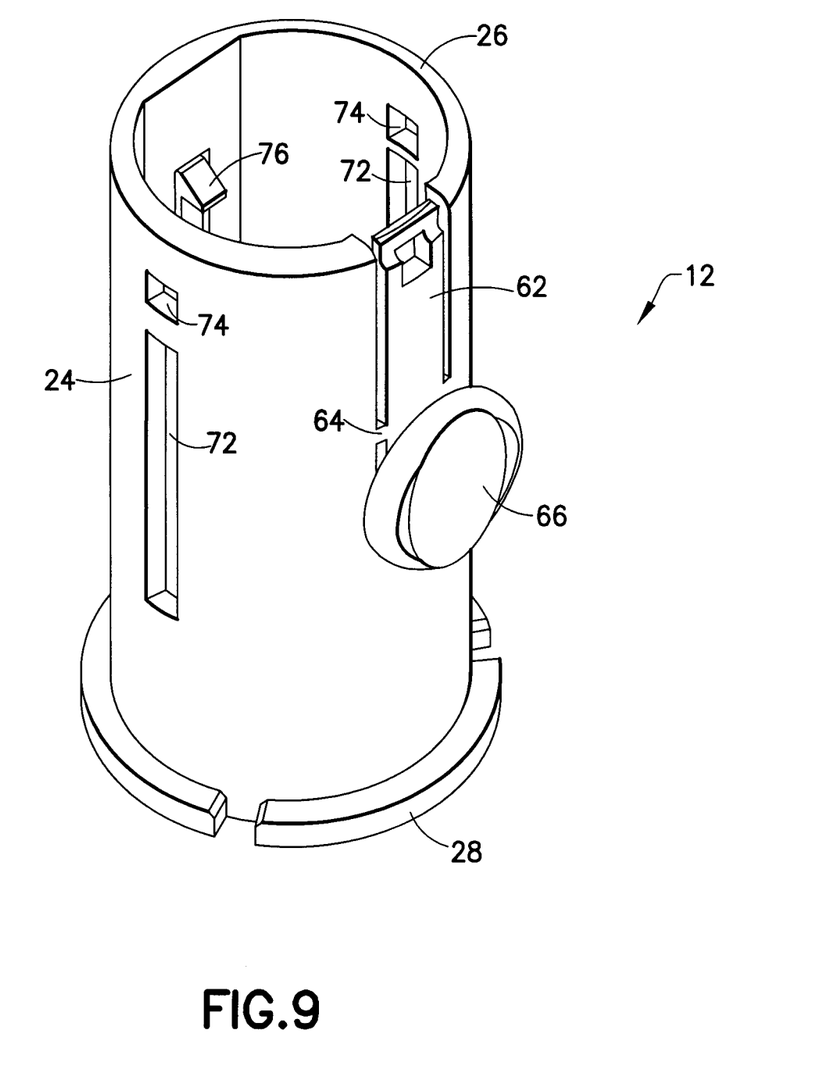
Figure 10:
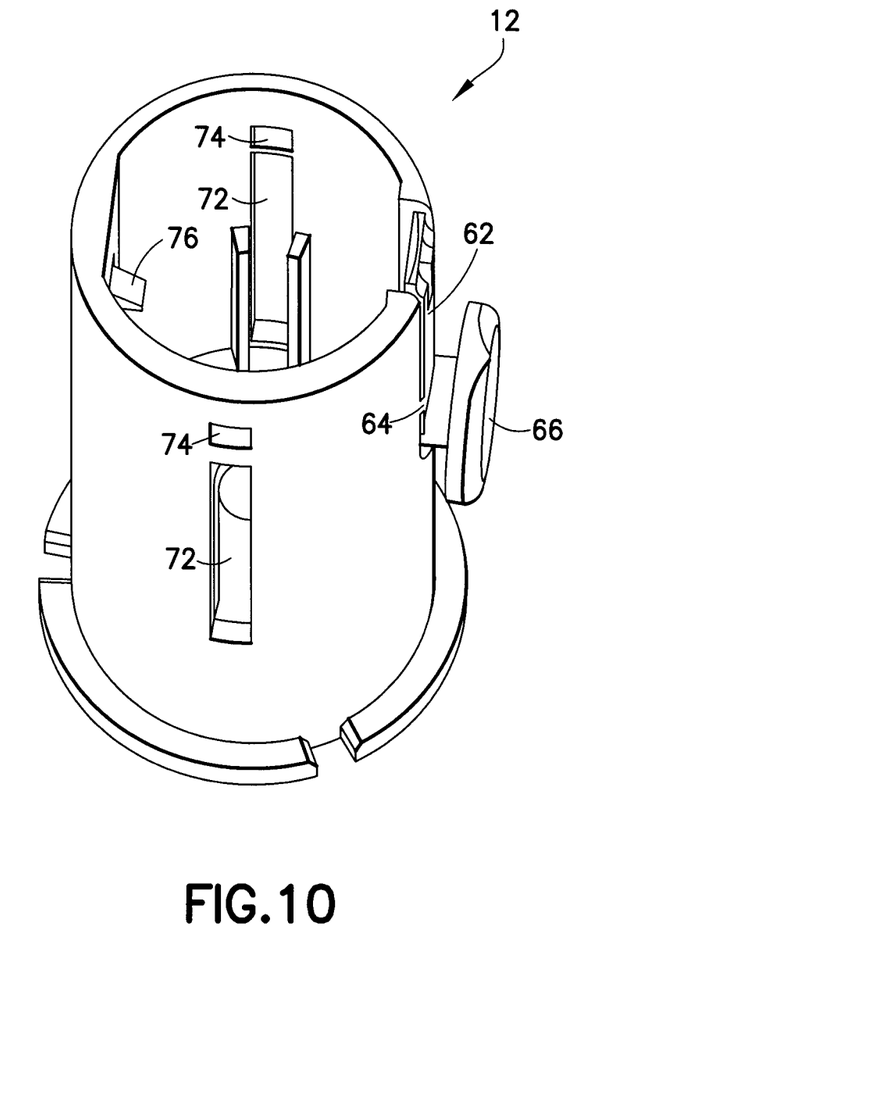
Figure 11:
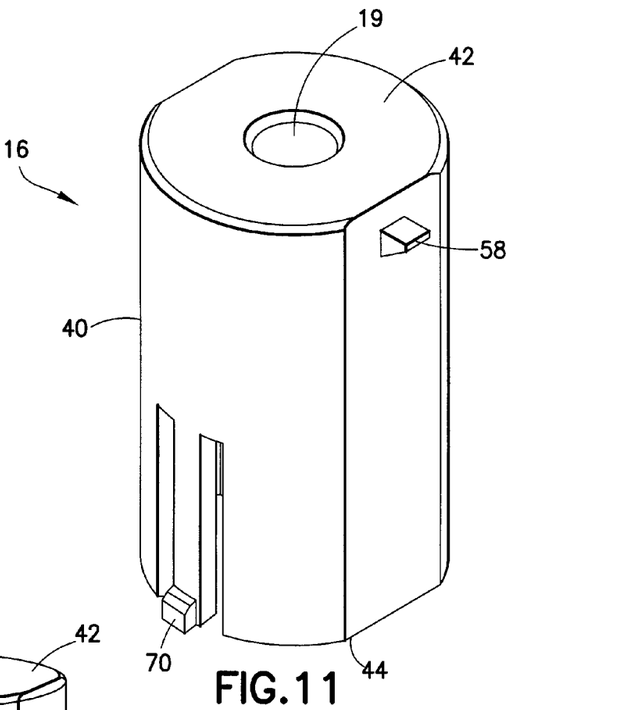
FIGS. 11-12 are different views of a shield usable with the subject invention; and, FIGS. 13-14 are different views of a needle hub usable with the subject invention.
Figure 12:
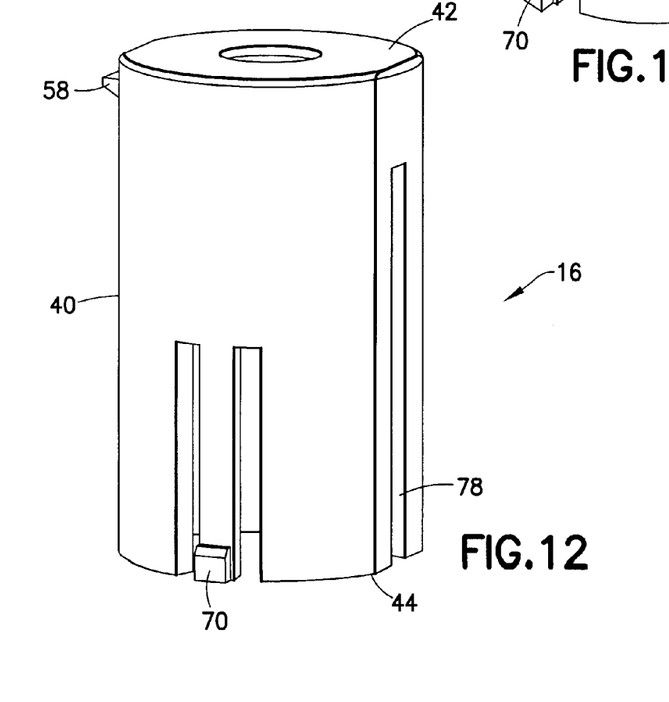

The shield 18 includes a body 40 having a distal end 42 and a proximal end 44. The shield 18 is configured to selectively cover the distal end 36 of the needle 16. As shown in FIGS. 1, 4 and 5 with the assembly 10 being in an initial state, the shield 18 does not cover the distal end 36 of the needle 16. An aperture 19 is formed through the distal end 42 which permits the needle 16 to pass therethrough with the shield 18 in the initial state. With reference to FIGS. 3, 6 and 7, in a shielded position, the shield 18 covers the distal end 36 of the needle 16.

The first and second biasing elements 20, 22 are each preferably a coil spring or compression spring. Other known biasing elements may be utilized with the subject invention. With reference to FIGS. 4 and 5, the needle hub 14 is shown in an initial position, wherein the needle 16 extends through the aperture 32 of the engagement wall 30. In addition, in the initial state, the shield 18 does not cover the distal end 36 of the needle 16. The first biasing element 20 is disposed to urge the needle hub 14 from the initial position to a second shielding position. Likewise, the second biasing element 22 is disposed to urge the shield 18 from the initial position to a second, shielded position. With reference to FIGS. 6 and 7, the needle hub 14 is shown in the second shielded position, wherein the proximal end 38 of the needle 16 is located distally of a proximally-facing surface 46 of the engagement wall 30. In addition, in the second state, the shield 18 covers the distal end 36 of the needle 16. In this manner, both the distal end 36 and the proximal end 38 of the needle 16 are covered to minimize possible inadvertent needle sticks therewith.

Figure 13:
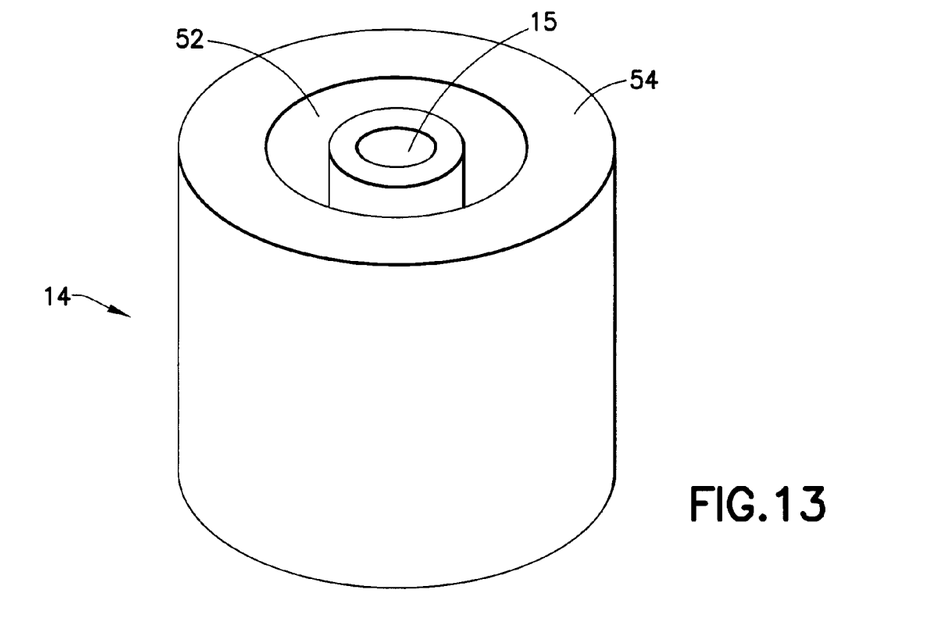
Figure 14:
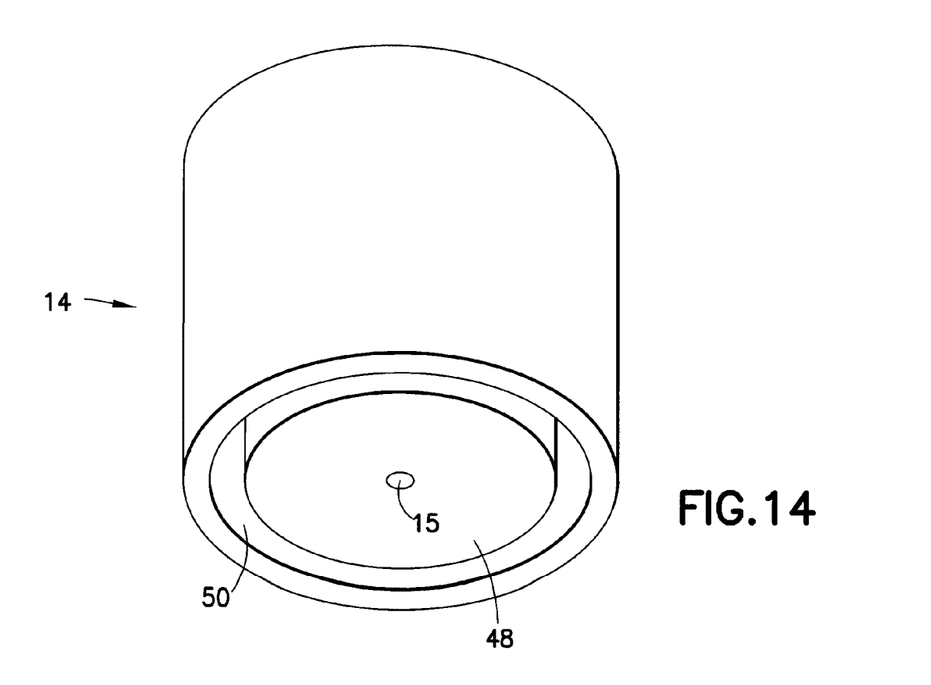

In a preferred arrangement, the first biasing element 20 is disposed between the engagement wall 30 and the needle hub 14 to urge the needle hub 14 in a distal direction away from the engagement wall 30. With reference to FIG. 14, a proximal face 48 of the needle hub 14 is shown which may be provided with a first retaining groove 50. The first biasing element 20 may be seated within the first retaining groove 50, as shown in FIGS. 4-7. The first retaining groove 50 may impart columnar rigidity to the first biasing element 20. In addition, the second biasing element 22 may be disposed between the needle hub 14 and the shield 18 so as to urge the shield 18 distally, away from the needle hub 14. With reference to FIG. 13, a second retaining groove 52 may be formed through a distal face 54 of the needle hub 14 in which the second biasing element 22 may be seated. A retaining collar 56 may be provided on the shield 18 which extends proximally from the distal end 42. The second biasing element 22 may circumscribe the retaining collar 56.

It is preferred that a locking arrangement be provided to releasably retain the needle hub 14 and the shield 18 in the initial state as shown in FIGS. 1, 4 and 5. A trigger activated locking arrangement may be utilized, in which a manual trigger is provided which, upon activation, releases the needle hub 14 and the shield 18 from the initial state, thereby permitting displacement to the shielded state, as shown in FIGS. 3, 6 and 7.

With reference to the figures, a locking arrangement may be provided which includes a detent 58 formed to extend from the body 40 of the shield 18. A locking aperture 60 is provided in the sidewall 24 of the carrier 12 formed to nestingly receive the detent 58, as shown in FIG. 4. The detent 58 and the locking aperture 60 are located to cooperate with the assembly 10 being in an initial state. The locking aperture 60 is located on a trigger arm 62 which is solely attached to the sidewall 24 at a fulcrum 64. A trigger button 66 is located on the trigger arm 62 proximally of the fulcrum 64. With a pressing force applied against the trigger button 66 as shown by arrow F in FIG. 4, the trigger button 66 causes the portion of the trigger arm 62 located proximally of the fulcrum 64 to deflect inwardly, thereby causing the portion of the trigger arm 62 located distally of the fulcrum 64 to deflect outwardly. Thus, with pressing force being applied against the trigger button 66, the trigger arm 62 may be displaced so that the locking aperture 60 is forced clear of the detent 58. The interengagement of the detent 58 and the locking aperture 60 provide a holding force for retaining the shield 18 in the initial state against the urging force of the first and second biasing elements 20, 22. The release of the detent 58 allows the second biasing element 22 to urge the shield 18 from the initial state to the shielded state.

The shield 18 also may be provided with one or more stop surfaces 68 for acting against the needle hub 14 in the initial state. As shown in FIG. 4, the stop surfaces 68 may be provided and positioned to prevent the needle hub 14 from moving distally from the initial state under force of the first biasing element 20. Thus, with the detent 58 being received within the locking aperture 60, the interengagement of the detent 58 and the locking aperture 60 provides resistance against movement of both the needle hub 14 and the shield 18. The detent 58 and the locking aperture 16 must be configured to resist the collective force generated by the first and second biasing elements 20, 22.

It is further preferred to provide the assembly 10 with a locking arrangement for locking the shield 18 in the shielded position. With reference to FIGS. 5 and 7, the shield 18 may be provided with one or more locking tabs 70. Corresponding guide slots 72 are formed in the sidewall 24 of the carrier 12. The guide slots allow the shield 18 to move distally with the locking tabs 70 translating therethrough. Snap-in locking holes 74 may be located distally of the guide slots 72 formed to nestingly receive the locking tabs 70, as shown in FIG. 7. Under force of the second biasing element 22, the locking tabs 70 may be resiliently forced to snap into the locking holes 74, thereby locking the shield 18 in a shielded position, as shown in FIG. 7.

The needle hub 14 need not be locked in the shielded position with the first biasing element 20 urging the needle hub 14 away from the engagement wall 30. One or more limits 76 may extend inwardly from the sidewall 24 to limit the allowable distal movement of the needle hub under force of the first biasing element 20. As shown in FIG. 6, the limits 76 are positioned to allow sufficient distal movement of the needle hub 14 such that the proximal end 38 of the needle 16 is located distally of the proximally-facing surface 46 of the engagement wall 30. By-pass slots 78 are formed in the shield 18 to receive the limits 76. The by-pass slots 78 allow the shield 18 to translate without impediment of the limits 76.

It is also understood that the shield 18 must be formed and positioned to cover the distal end 36 of the needle 16 in the shielded position with the needle hub 14 having been repositioned distally from its initial state. In other words, the distal end 36 of the needle 16 is located distally further from the engagement wall 30 than in the initial position.

What is claimed is:

1. A safety pen needle assembly comprising:

a tubular carrier having a distal end, a proximal end and a transverse engagement wall located between said proximal and distal ends, said engagement wall having a proximally-facing outer surface and an aperture formed through said engagement wall;

a needle having a distal end, for injection into a patient, and a proximal end;

a needle hub, said needle being fixed to said needle hub so as to move therewith, said needle hub being disposed in said carrier distally of said engagement wall;

a shield for selectively covering said distal end of said needle;

a first biasing means for urging said needle hub from a first hub position where said needle extends through said aperture of said engagement wall to a second hub position where said proximal end of said needle is located distally of said proximally-facing outer surface of said engagement wall;

a second biasing means for urging said shield from a first shield position where said distal end of said needle is not covered by said shield to a second shield position where said distal end of said needle is covered by said shield; and, a locking means for releasably retaining said shield in said first shield position, wherein upon a release of said locking means, said second biasing means urges said shield from said first shield position to said second shield position.

2. The assembly as in claim 1, wherein, with said shield being retained in said first shield position, said hub is retained in said first hub position.

3. The assembly as in claim 1, wherein, with said release of said locking means, said shield being urged to said second shield position by said second biasing means and said first biasing means urging said hub to said second hub position.

* * * * *